United States Patent [19]

Mullenbach et al.

[11] Patent Number: 5,547,935
[45] Date of Patent: Aug. 20, 1996

[54] MUTEINS OF HUMAN EPIDERMAL GROWTH FACTOR EXHIBITING ENHANCED BINDING AT LOW PH

[75] Inventors: Guy T. Mullenbach, San Francisco; Jeffrey M. Blaney; Steven Rosenberg, both of Oakland, all of Calif.

[73] Assignee: Chiron Corporation, Emeryville, Calif.

[21] Appl. No.: 284,923

[22] Filed: Aug. 2, 1994

Related U.S. Application Data

[63] Continuation of Ser. No. 746,651, Aug. 16, 1991, abandoned.

[51] Int. Cl.$^6$ .................... C12N 15/18; A61K 38/18; C07K 14/485
[52] U.S. Cl. .................... 514/12; 530/324; 536/23.5
[58] Field of Search .................... 514/2, 12; 530/399, 530/324; 435/320.1, 255, 252.33; 536/27, 23.5

[56] References Cited

U.S. PATENT DOCUMENTS

| | | | |
|---|---|---|---|
| 3,917,824 | 11/1975 | Camble et al. | 424/177.1 |
| 3,948,875 | 4/1976 | Cohen et al. | 260/112 |
| 4,528,186 | 7/1985 | Nishimura et al. | 424/99 |
| 4,621,052 | 11/1986 | Sugimoto | 435/68 |
| 4,686,283 | 8/1987 | Nestor, Jr. et al. | 530/327 |
| 4,703,108 | 10/1987 | Silver et al. | 530/356 |
| 4,717,717 | 1/1988 | Finkenaur | 514/21 |
| 4,743,679 | 5/1988 | Cohen et al. | 530/530 |
| 5,096,825 | 3/1992 | Barr et al. | 435/255 |
| 5,130,298 | 7/1992 | Cini et al. | 514/12 |
| 5,158,935 | 10/1992 | Nascimento et al. | 514/12 |

FOREIGN PATENT DOCUMENTS 46039  2/1982  European Pat. Off. .

OTHER PUBLICATIONS

Moy, F. J. et al., *PNAS*, 86: 9836–9840, 1989.
Hommel, U. et al., *Biochemistry*, 30: 8891–8898, 1991 (Sep.).
Gregory and Preston, 1977, *Int. J. Peptide Protein Res.* 9:107–118.
Carpenter and Cohen, 1979, *Ann. Rev. Biochem.* 48:193–216.
Urdea et al., 1983, *Proc. Natl. Acad. Sci. USA* 80:7461–7465.
Oka et al., 1985, *Proc. Natl. Acad. Sci. USA* 82:7212–7216.
Makino et al., 1987, *Proc. Natl. Acad. Sci. USA* 84:7841–7845.
George–Nascimento et al., 1988, *Biochem.* 27:797–802.

*Primary Examiner*—Marianne P. Allen
*Attorney, Agent, or Firm*—Paul B. Savereide, Ph.D.; Amy L. Collins, Ph.D.; Robert P. Blackburn

[57] ABSTRACT

EGF muteins in which the histidine at position 16 is replaced with a neutral or acidic amino acid exhibit activity at pHs lower than obtainable with wild type EGF.

5 Claims, 1 Drawing Sheet

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 53 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

```
Asn  Ser  Asp  Ser  Glu  Cys  Pro  Leu  Ser  His  Asp  Gly  Tyr  Cys  Leu  His
1                 5                                 10                                1 5

Asp  Gly  Val  Cys  Met  Tyr  Ile  Glu  Ala  Leu  Asp  Lys  Tyr  Ala  Cys  Asn
```

|  | 20 | 25 | 30 |
|---|---|---|---|

Cys Val Val Gly Tyr Ile Gly Glu Arg Cys Gln Tyr Arg Asp Leu Lys
      35                    40                    45

Trp Trp Glu Leu Arg
 50

(2) INFORMATION FOR SEQ ID NO:2:

(i) SEQUENCE CHARACTERISTICS:
      (A) LENGTH: 53 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:2:

Asn Ser Tyr Pro Gly Cys Pro Ser Ser Tyr Asp Gly Tyr Cys Leu Asn
 1               5                   10                   15

Gly Gly Val Cys Met His Ile Glu Ser Leu Asp Ser Tyr Thr Cys Asn
          20                  25                  30

Cys Val Ile Gly Tyr Ser Gly Asp Arg Cys Gln Thr Arg Asp Leu Arg
         35                 40                  45

Trp Trp Glu Leu Arg
 50

MUTEINS OF HUMAN EPIDERMAL GROWTH FACTOR EXHIBITING ENHANCED BINDING AT LOW PH

This application is a continuation of application Ser. No. 07/746,651, filed 16 Aug. 1991 now abandoned.

DESCRIPTION

1. Technical Field

This invention relates to the molecular biology of cellular growth factors and recombinant DNA technology. More specifically, this invention relates to epidermal growth factor (EGF) modified to increase its binding activity at low pH, and the therapeutic uses of modified EGF of the invention.

2. Background of the Invention

Epidermal growth factor (EGF) is a 53-amino acid protein synthesized in the duodenum and salivary glands of normal humans, and normally excreted in the urine. For its effect in reducing gastric acid secretion, and its first isolation source, it was formerly termed urogastrone. After it was sequenced, it was recognized that urogastrone was homologous to murine EGF, and that urogastrone additionally stimulated the proliferation of certain cell types, prompting a change in nomenclature to EGF. The biological and chemical properties of hEGF and mEGF are reviewed in G. Carpenter et al, *Ann Rev Biochem* (1979) 48:193–216.

The aminio acid sequence of human EGF is:

| Asn | Ser | Asp | Ser | Glu | Cys | Pro | Leu | Ser | His |
|---|---|---|---|---|---|---|---|---|---|
| Asp | Gly | Tyr | Cys | Leu | His | Asp | Gly | Val | Cys |
| Met | Tyr | Ile | Glu | Ala | Leu | Asp | Lys | Tyr | Ala |
| Cys | Asn | Cys | Val | Val | Gly | Tyr | Ile | Gly | Glu |
| Arg | Cys | Gln | Tyr | Arg | Asp | Leu | Lys | Trp | Trp |
| Glu | Leu | Arg | (SEQ ID NO: 1) | | | | | | |

This sequence was published by H. Gregory et al, *Int J Peptide Protein Res* (1977) 107–18, who isolated the protein as urogastrone from human urine (1 mg/1000 L), and disclosed its sequence homology with mEGF. Murine EGF has the sequence (differences from hEGF underlined):

| Asn | Ser | Tyr | Pro | Gly | Cys | Pro | Ser | Ser | Tyr |
|---|---|---|---|---|---|---|---|---|---|
| Asp | Gly | Tyr | Cys | Leu | Asn | Gly | Gly | Val | Cys |
| Met | His | Ile | Glu | Ser | Leu | Asp | Ser | Tyr | Thr |
| Cys | Asn | Cys | Val | Ile | Gly | Tyr | Ser | Gly | Asp |
| Arg | Cys | Gln | Thr | Arg | Asp | Leu | Arg | Trp | Trp |
| Glu | Leu | Arg | (SEQ ID NO: 2), | | | | | | | which conserves the disulfide bonds. Gregory also discloses that urogastrone may be maintained in aqueous solution at pHs of 1–11 for at least 20 hours without loss of activity, and that the six C-terminal amino acids may be removed without loss of biological activity.

Preparation of an hEGF gene is described in EPO 046,039, and cloning and expression of EGF is disclosed in commonly-owned U.S. patent application Ser. No. 004,212, filed 5 Jan. 1987, a continuation of Ser. No. 457,412, filed 12 Jan. 1983, now abandoned. U.S. Ser. No. 004,212 is incorporated herein by reference in full. Other disclosures of EGF preparation are M. S. Urdea et al, *Proc Nat Acad Sci USA*, (1983) 80:7461–65 (chemical synthesis of gene and expression in yeast), T. Oka et al, *Proc Nat Acad Sci USA*, (1985) 82:7212–16 (fusion protein in E. coli); Cohen et al, U.S. Pat. No. 4,743,679 (recombinant fusion protein); Sugimoto, U.S. Pat. No. 4,621,052 (human hybridoma cell culture); Nishimura et al, U.S. Pat. No. 4,528,186 (adsorption from urine); and Cohen et al, U.S. Pat. No. 3,948,875 (purification from murine submaxillary glands). Pharmaceutical compositions containing EGF are disclosed in Finkenaur, U.S. Pat. No. 4,717,717 (stabilized against degradation by moisture with water-soluble cellulose derivatives); U.S. Pat. No. 4,703,108 (cross-linked collagen sponge); and Camble et al, U.S. Pat. No. 3,917,824 (lyophilized solid or dextrose solution).

C. George-Nascimento et al, *Biochem* (1988) 27:797–802 reported the isolation from recombinant yeast culture of four distinct forms of EGF, termed A, B, C, and D, each of which exhibit full EGF activity. EGF-D represents the 52-amino acid sequence obtained by removing the C-terminal arg, while EGF-B corresponds to EGF-D wherein the C-terminal arg-leu has been removed. EGF-C appears to be EGF-D in which $Met_{21}$ has been oxidized, while EGF-A appears to be EGF-B with Met21 oxidized. EGF-D is reported to be stable when stored as a lyophilized powder.

George-Nascimento et al, U.S. Ser. No. 07/351,773 disclosed EGF muteins in which the $Asp_{11}$ residue is replaced, preferably with Glu, in order to prevent degradation by isomerization of the Asp residue. $Asp_{11}$ may isomerize to iso-Asp, which disturbs the peptide backbone and impairs the peptide's activity.

The physical structure of a recombinantly-produced hEGF has been partially elucidated using COSY and NOESY by K. Makino et al, *Proc Nat Acad Sci USA* (1987) 84:7841–45. Makino disclosed that amino acids 19–32 form an antiparallel beta-pleated sheet, placing $His_{10}$ in close proximity to $Tyr_{22}$ and $Tyr_{29}$. Makino also suggested that amino acids 45–53 may form an alpha helix which crosses the surface of the beta-pleated sheet, creating a hydrophobic pocket comprising $His_{10}$, $Tyr_{22}$, $Tyr_{29}$, $Trp_{49}$, and $Trp_{50}$. Removal of amino acids 49–53 altered the NMR chemical shift and pKa of the ring protons on $His_{10}$, $His_{19}$, $Tyr_{22}$, and $Tyr_{29}$, and drastically reduced the activity, suggesting that these amino acids may participate in the EGF binding site.

Nestor et al, U.S. Pat. No. 4,686,283 disclosed the preparation of polypeptides and polypeptide analogs homologous to amino acids 34–43 of EGF and TGF-α, which are useful as EGF antagonists and for preparing anti-EGF antibodies.

DISCLOSURE OF THE INVENTION

Contrary to the teachings in the art, we have found that $His_{16}$ is not a residue essential for receptor binding activity. Surprisingly, we discovered that EGF muteins in which $His_{16}$ is replaced with a neutral or acidic amino acid exhibit activity equal or superior to wild-type EGF at neutral and basic pH, and which retain their activity at pHs as low as 4.0, whereas wtEGF exhibits substantially reduced binding activity below pH 6.5.

We have now invented EGF muteins having neutral or acidic residues at position 16, which exhibit activity at low pH which is enhanced with respect to wild-type EGF. We have also invented therapeutic methods of treatment comprising administering the EGF muteins of the invention to a subject in need thereof.

MODES OF CARRYING OUT THE INVENTION

Definitions

Figure 1:
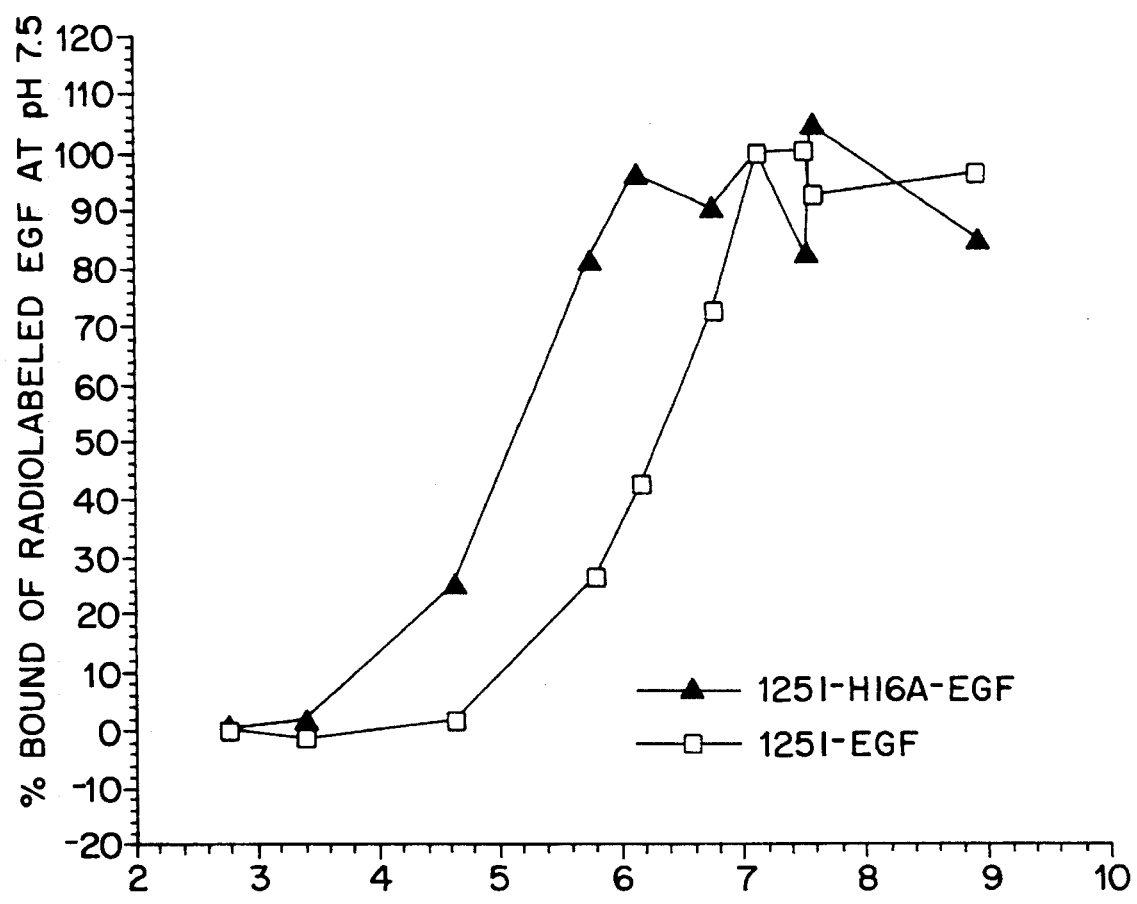
FIG. 1 graphically depicts the binding of labeled wtEGF and EGF-$A_{16}$ to fixed A431 cells as a function of pH.

The term "EGF" as used herein refers to a polypeptide having substantially the same sequence and activity as purified native epidermal growth factor. The term "hEGF" denotes the EGF protein having the substantially the same sequence and characteristics as epidermal growth factor obtained from humans, while "rhEGF" specifies that the hEGF is produced by recombinant methods. Similarly, "mEGF" denotes EGF of murine origin, and "rmEGF" denotes EGF having the murine sequence prepared by recombinant means. "wtEGF" specifies EGF having the wild-type (naturally occurring) sequence. "EGF mutein" specifies an EGF peptide having a sequence different from wild type. EGF muteins will have from 1 to 20 differences from the wild type amino acid sequence.

"EGF" includes proteins varying from the native sequence, e.g., by substitution of one or more amino acids with other amino acids, so long as the EGF biological activity is substantially preserved. EGF biological activity is preferably measured by a receptor binding assay. "Substantially similar" sequences are those which preferably have at least 65 number % homology with the native sequence, more preferably about 85 number %, still more preferably about 90 number %, and most preferred about 95 number %. Thus, for example, a human EGF protein in which the methionine (Met) at position 21 is replaced with isoleucine (Ile) falls within the scope of "EGF." Such a protein is denoted hEGF-$I_{21}$ generally, and is denoted rhEGF-$I_{21}$ if prepared recombinantly (chemically synthesized hEGF is included in the term "hEGF"). Similarly, hEGF having the Asp at position 11 replaced with Glu is denoted hEGF-$E_{11}$. Some EGF proteins truncated near the carboxy terminal retain their biological activity, and are denoted with a subscript indicating the last peptide residue retained. Thus, EGF lacking the last 2 of its normal 53 peptides is indicated EGF$_{51}$. Proteins having an amino acid deletion, for example wherein Trp49 is absent, are denoted with the term "del" (or Δ) and a subscript indicating the position, without altering the numbering of the remaining amino acids. Thus, if Trp$_{49}$ were deleted, the resulting protein would be indicated EGF-$\Delta_{49}$. Insertions, increasing the chain length, are indicated as substitutions substituting 2 or more amino acids for one, e.g., rhEGF-L/G$_{15}$ indicates insertion of Gly after the natural Leu$_{15}$. Finally, an EGF of the invention where His$_{16}$ has been replaced by another amino acid, with or without other modifications, is denoted generically by EGF-$X_{16}$.

The term "amino acid" as used herein refers generally to a molecule of the formula NH$_2$—CHR—COOH, wherein R is a side chain or residue which may or may not occur naturally. The terms "natural amino acid" and "naturally-occurring amino acid" refer to those 20 amino acids which are the normal constituents of proteins, e.g., Ala, Asp, Cys, Glu, Phe, Gly, His, Ile, Lys, Leu, Met, Asn, Pro, Gln, Arg, Ser, Thr, Val, Trp, Tyr. Other (non-natural) amino acids which may be used include homoserine, phenylglycine, taurine, iodotyrosine, and the like. Preferably, the side chain (R) of an amino acid will contain 1–12 carbon atoms, 0–4 nitrogen atoms, 0–2 sulfurs, 0–4 oxygens, and 0–4 halogen atoms.

A "condition treatable with EGF" is any disorder or wound having symptoms which may be ameliorated using EGF. For example, EGF is known to reduce secretion and oversecretion of gastric acid. Accordingly, EGF-$X_{16}$ may be used to treat gastric and duodenal ulcers, as well as gastric hyperacidity. EGF is also known to improve healing of epithelial wounds, including wounds to the eye, e.g., caused by trauma (including surgery), infection, and the like. Accordingly, EGF-$X_{16}$ may be administered to epithelial wounds to improve wound healing. EGF-$X_{16}$ is particularly useful in corneal storage media, for preserving the epithelial and endothelial cell layers on corneal explants stored for subsequent transplantation. As corneal explants may be stored for period of up to about three months, it is extremely useful to use a form of EGF which is not chemically degraded over that time period.

General Method

The proteins of the present invention are muteins of EGF, preferably human EGF, in which the His residue at position 16 is replaced with a neutral or acidic amino acid. Neutral amino acids include, without limitation, Ala, Gly, Val, Leu, Ile, Met, Ser, Thr, Phe, Tyr, Trp, homo-alanine, benzylglycine, and the like. Presently preferred neutral amino acids are Ala, Gly, Val, Ser, and Thr. Acidic amino acids include, without limitation, Asp, Glu, homoglutamic acid, and the like. The presently preferred acidic amino acids are Asp and Glu. It is believed that His$_{16}$ does not participate in receptor binding, but does interfere with receptor binding when protonated at low pH. This is likely due to the positive charge acquired with protonation. Thus, peptides in accordance with the present invention lack a basic residue at position 15. Any amino acid which is not easily protonated at low pH, and which does not stearically interfere with binding, may be substituted for His$_{16}$ with a reasonable expectation of success.

As disclosed by C. George-Nascimento et al. in copending application U.S. Ser. No. 004,212, the Asp$_{11}$ residue of hEGF is prone to isomerization in solution, resulting in the loss of EGF biological activity. George-Nascimento demonstrated that other amino acids (such as Glu) may be substituted for Asp$_{11}$, significantly increasing the shelf life of the peptide without loss of biological activity. Such modifications are also useful to the peptides of the present invention. Thus, derivatives such as rhEGF-$E_{11}A_{16}$ are within the scope of this invention.

We have also found that substitutions at positions 12 and 13 result in EGF muteins exhibiting increased receptor affinity and/or mitogenicity. Presently preferred substitutions are Trp for Tyr$_{13}$ and Glu for Gly$_{12}$. Thus, preferred peptides of the invention include EGF-$E_{12}A_{16}$, EGF-$W_{13}A_{16}$, EGF-$E_{12}W_{13}A_{16}$, EGF-$E_{11}E_{12}A_{16}$, EGF-$E_{11}E_{12}W_{13}A_{16}$, and the like. Peptides substituted at positions 12 and/or 13 but lacking substitutions of the invention at position 16 may be used where activity at low pH is not critical, and still exhibit the enhanced levels of activity at neutral pH. Thus, peptides such as EGF-$E_{12}$, EGF-$W_{13}$, and EGF-$E_{12}W_{13}$ are also useful.

Peptides of the invention are EGF muteins having a neutral or acidic substitution at position 16, and which preferably are additionally substituted at positions 11, 12, and/or 13. Other positions, such as $Glu_{43}$, may also be substituted without detrimental effect on EGF activity. In general, critical residues are typically conserved across species lines, whereas non-critical residues are more likely to vary from one species to the next. Thus, one may compare EGF sequences obtained from differing species for guidance as to which residues may be varied without loss of activity. Both human and murine EGF exhibit activity with human cells. Thus, non-conserved positions indicate residues which are not essential for binding to human EGF receptors. These residues are 3–5, 8, 10, 16–17, 22, 25, 28, 30, 35, 38, 40, 44 and 48. Some or all of these positions may be altered, within reason, without loss of biological activity. Such alteration is preferably a conservative amino acid substitution, such as Gly for Ala, Val or Leu for Ile, Asp for Glu, Gln for Asn, and so forth, in which basic residues are replaced with other basic residues, acidic residues are replaced with other acidic residues, etc. It is preferred not to change Pro residues due to the effect on the polypeptide backbone.

EGF may also be altered by adding an N-terminal extension. EGF-flag ($\phi$EGF) derivatives have the additional sequence DWKDDDDK, which permits rapid purification of peptides by affinity chromatography on anti-flag MAb columns (International Biotechnology Inc.). EGF-flag derivatives are also biologically active, particularly $\phi$EGF-$E_{12}$ and $\phi$EGF-$W_{13}$.

The proteins of the invention may be prepared by traditional chemical means, by recombinant means, or by a combination of both methods. The 53 amino acid length of EGF is within the practical limits for use of commercially available peptide synthesizers, which comprises the most convenient method for preparing those EGF-$X_{16}$ derivatives of the invention which contain non-natural amino acids. The use of such commercial machines is well-known in the art, and needs no further description.

However, recombinant methods of production are currently more economical, and more amenable to commercial manufacture. Further, recombinant expression in eukaryotic cells (e.g., yeast) generally provides EGF which is correctly folded and disulfide-linked.

Expression

The proteins of the invention may be expressed in either prokaryotic or eukaryotic systems, or in in vitro expression systems. Prokaryotes are most frequently represented by various strains of E. coli. However, other microbial strains may also be used, such as bacilli (for example *Bacillus subtilis*), various species of Pseudomonas, and other bacterial strains. In such prokaryotic systems, plasmid vectors which contain replication sites and control sequences derived from a species compatible with the host are use. For example, E. coli is typically transformed using derivatives of pBR322, a plasmid derived from an E. coli species by Bolivar et al, *Gene* (1977) 2:95. Commonly used prokaryotic control sequences, which are defined herein to include promoters for transcription initiation, optionally with an operator, along with ribosome binding site sequences, include such commonly used promoters as the β-lactamase (penicillinase) and lactose (lac) promoter systems (Chang et al, *Nature* (1977) 198:1056) and the tryptophan (trp) promoter system (Goeddel et al, *Nuc Acids Res* (1980) 8:4057) and the lambda-derived $P_L$ promoter and N-gene ribosome binding site (Shimatake et al, *Nature* (1981) 292:128). However, any available promoter system compatible with prokaryotes can be used.

The expression systems useful in eukaryotic systems of the invention comprise promoters derived from appropriate eukaryotic genes. A class of promoters useful in yeast, for example, include promoters for synthesis of glycolytic enzymes, including those for 3-phosphoglycerate kinase (Hitzeman et al, *J Biol Chem* (1980) 255:2073), and especially glyceraldehyde 3-phosphate dehydrogenase (GAPDH) (M. S. Urdea et al, *Proc Nat Acad Sci USA* (1983) 80:7461–65). Other promoters include those from the enolase gene (M. J. Holland et al, *J Biol Chem* (1981) 256:1385) or the Leu2 gene obtained from YEp13 (J. Broach et al, *Gene* (1978) 8:121). Yeast is the presently preferred expression host.

Suitable mammalian promoters include the early and late promoters from SV40 (Fiers et al, *Nature* (1978) 273:113) and other viral promoters such as those derived from polyoma, adenovirus II, bovine papilloma virus, or avian sarcoma viruses. Suitable viral and mammalian enhancers are cited above. In the event plant cells are used as an expression system, the nopaline synthesis promoter is appropriate (A. Depicker et al, *J Mol Appl Gen* (1982) 1:561). Expression in insect cell culture may conveniently be achieved using a baculovirus vector, for example, transfer vectors derived from the baculovirus *Autographa californica* nuclear polyhedrosis virus (AcNPV), (see PCT WO89/046699).

One may express rEGF-$X_{16}$ in vitro, and incorporate "non-natural" amino acids using the technique disclosed by C. J. Noren et al, *Science* (1989) 244:182–88. Briefly, an in vitro expression vector is prepared (e.g., an sp6 plasmid), and the codon position corresponding to the non-natural amino acid site is altered to a nonsense codon (particularly TAG), e.g., using oligonucleotide-directed mutagenesis. A corresponding tRNA is prepared and acylated in vitro with the desired non-natural amino acid (e.g., 4-fluorophenylalanine, phenylglycine, and the like). Expression of the altered vector in a cell-free system in the presence of the acylated tRNA provides the polypeptide incorporating the non-natural amino acid.

Transformation

Depending on the host cell used, transformation is done using standard techniques appropriate to such cells. The calcium treatment employing calcium chloride, as described by S. N. Cohen, *Proc Nat Acad Sci USA* (1972) 69:2110, or the RbCl method described in Maniatis et al, *Molecular Cloning: A Laboratory Manual* (1982) Cold Spring Harbor Press, p. 254, is used for prokaryotes or other cells which contain substantial cell wall barriers. Infection with *Agrobacterium tumefaciens* (C. H. Shaw et al, *Gene* (1983) 23:315) is used for certain plant cells. For mammalian cells without cell walls, the calcium phosphate precipitation method of Graham and van der Eb, *Virology* (1978) 52:546 is preferred. Alternatively, one may use a liposomal formulation for transfection. A synthetic lipid useful for polynucleotide transfection is N-[1-(2,3-dioleyloxy)propyl]-N,N,N-trimethylammonium chloride, which is commercially available under the name Lipofectin® (available from BRL, Gaithersburg, Md.), and is described by P. L. Felgner et al, *Proc Nat Acad Sci USA* (1987) 84:7413. Transformations into yeast are carried out according to the method of P. Van Solingen et al, *J Bacter* (1977) 130:946 and C. L. Hsiao et al, *Proc Nat Acad Sci USA* (1979) 76:3829.

Probing cDNA or Genomic Libraries cDNA or genomic libraries are screened using the colony hybridization procedure. Each microtiter plate is replicated onto duplicate nitrocellulose filter papers (S & S type BA-85) and colonies are allowed to grow at 37° C. for 14–16 hr on L agar containing 50 pg/mL Amp. The colonies are lysed and DNA fixed to the filter by sequential treatment for 5 min with 500 mM NaOH, 1.5 M NaCl, and are washed twice for 5 rain each time with 5× standard saline citrate (SSC). Filters are air dried and baked at 80° C. for 2 hr. The duplicate filters are prehybridized at 42° C. for 6–8 hr with 10 mL per filter of DNA hybridization buffer (5× SSC, pH 7.0, 5× Denhardt's solution (polyvinylpyrrolidone, ficoll, and bovine serum albumin; 1×=0.02% of each), 50 mM sodium phosphate buffer at pH 7.0, 0.2% SDS, 20 μg/mL poly-U, and 50 μg/mL denatured salmon sperm DNA).

The samples are hybridized with kinased probe under conditions which depend on the stringency desired. Typical moderately stringent conditions employ a temperature of 42° C. for 24–36 hr with 1–5 mL/filter of DNA hybridization buffer containing probe. For higher stringencies, high temperatures and shorter times are employed. The filters are washed four times for 30 min each time at 37° C. with 2× SSC, 0.2% SDS and 50 mM sodium phosphate buffer at pH 7, then washed twice with 2× SSC and 0.2% SDS, air dried, and are autoradiographed at −70° C. for 2 to 3 days.

Vector Construction

Construction of suitable vectors containing the desired coding and control sequences employs standard ligation and restriction techniques which are well understood in the art. Isolated plasmids, DNA sequences, or synthesized oligonucleotides are cleaved, tailored and religated in the form desired.

Site specific DNA cleavage is performed by treatment with a suitable restriction enzyme (or enzymes) under conditions which are generally understood in the art, generally following the manufacturer's directions. See, e.g., New England Biolabs, Product Catalog. In general, about 1 μg of plasmid or DNA sequence is cleaved by one unit of enzyme in about 20 μL of buffer solution; in the examples herein, typically, an excess of restriction enzyme is used to insure complete digestion of the DNA substrate. Incubation times of about 1 hr to 2 hr at about 37° C. are workable, although variations can be tolerated. After each incubation, protein is removed by extraction with phenol/chloroform, and may be followed by diethyl ether extraction, and the nucleic acid recovered from aqueous fractions by ethanol precipitation followed by separation over a Sephadex® G-50 spin column. If desired, size separation of the cleaved fragments may be performed by polyacrylamide gel or agarose gel electrophoresis using standard techniques. A general description of size separations is found in *Meth Enzymol* (1980) 65:499–560.

Restriction cleaved fragments may be blunt ended by treating with the large fragment of E. coli DNA polymerase I (Klenow) in the presence of the four deoxyribonucleotide triphosphates (dNTPs) using incubation times of about 15 to 25 min at 20° to 25° C. in 50 mM Tris, pH 7.6, 50 mM NaCl, 6 mM MgCl$_2$, 6 mM DTT and 5–10 μM dNTPs. The Klenow fragment fills in at 5' sticky ends but chews back protruding 3' single strands, even though the four dNTPs are present. If desired, selective repair can be performed by supplying only 1–3 of the dNTPs, within the limitations dictated by the nature of the sticky ends. After treatment with Klenow fragment, the mixture is extracted with phenol/chloroform and ethanol precipitated followed by running over a Sephadex® G-50 spin column. Treatment under appropriate conditions with S1 nuclease results in hydrolysis of any single-stranded portion.

Synthetic oligonucleotides are prepared by the triester method of Matteucci et al, *J Am Chem Soc* (1981) 103:3185, or using commercially available automated oligonucleotide synthesizers. Kinasing of single strands prior to annealing or for labeling is achieved using an excess, e.g., approximately 10 units of polynucleotide kinase to 0.1 nmole substrate in the presence of 50 mM Tris, pH 7.6, 10 mM MgCl$_2$, 5 mM DTT, 1–2 mM ATP, 1.7 pmoles $^{32}$P-ATP (2.9 mCi/mmole), 0.1 mM spermidine, and 0.1 mM EDTA.

Ligations are performed in 15–30 μL volumes under the following standard conditions and temperatures: 20 mM Tris-HCl, pH 7.5, 10 mM MgCl$_2$, 10 mM DTT, 33 μg/mL BSA, 10 mM-50 mM NaCl, and either 40 μM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 1 μg/mL total DNA concentrations (5–100 nM total end concentration). Intermolecular blunt end ligations (usually employing a 10–30 fold molar excess of linkers) are performed at 1 pM total ends concentration.

In vector construction employing "vector fragments", the vector fragment is commonly treated with bacterial alkaline phosphatase (BAP) in order to remove the 5' phosphate and prevent religation of the vector. BAP digestions are conducted at pH 8 in approximately 150 mM Tris, in the presence of Na$^+$ and Mg$^{2+}$ using about 1 unit of BAP per μg of vector at 60° C. for about 1 hr. In order to recover the nucleic acid fragments, the preparation is extracted with phenol/chloroform and ethanol precipitated and desalted by application to a Sephadex® G-50 spin column. Alternatively, religation can be prevented in vectors which have been double digested by additional restriction enzyme digestion of the unwanted fragments.

For portions of vectors derived from cDNA or genomic DNA which require sequence modifications, site specific primer directed mutagenesis may be used. This is conducted using a synthetic oligonucleotide primer complementary to a single-stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having the mutated form as a single strand; 50% will have the original sequence. The resulting plaques are hybridized with kinased synthetic primer under allele-specific conditions. In general, one may vary the temperature, ionic strength, and concentration of chaotropic agent(s) in the hybridization solution to obtain conditions under which substantially no probes will hybridize in the absence of an "exact match." For hybridization of probes to bound DNA, the empirical formula for calculating optimum temperature under standard conditions (0.9 M NaCl) is $$T(°C.) = 4(N_G + N_C) + 2(N_A + N_T) - 5° C.,$$

where $N_G$, $N_C$, $N_A$, and $N_T$ are the numbers of G, C, A, and T bases in the probe (J. Meinkoth et al, *Anal Biochem* (1984) 138:267–84). Plaques which hybridize with the probe are then picked, cultured, and the DNA recovered.

Verification of Construction

Correct ligations for plasmid construction may be confirmed by first transforming E. coli strain MM294 obtained from E. coli Genetic Stock Center, CGSC #6135, or other suitable host with the ligation mixture. Successful transformants are selected by ampicillin, tetracycline or other antibiotic resistance or using other markers depending on the plasmid construction, as is understood in the art. Plasmids from the transformants are then prepared according to the method of D. B. Clewell et al, *Proc Nat Acad Sci USA* (1969) 62:1159, optionally following chloramphenicol amplification (D. B. Clewell, *J Bacteriol* (1972) 10:667). The isolated DNA is analyzed by restriction and/or sequenced by the dideoxy method of F. Sanger et al, *Proc Nat Acad Sci USA* (1977) 74:5463 as further described by Messing et al, *Nuc Acids Res* (1981) 9:309, or by the method of Maxam and Gilbert, *Meth Enzymol* (1980) 65:499.

Administration

EGF-$X_{16}$ is preferably administered orally, topically, or by parenteral means, including subcutaneous and intramuscular injection, implantation of sustained release depots, intravenous injection, intranasal administration, and the like. When used to treat trauma, it may be advantageous to apply EGF-$X_{16}$ directly to the wound, e.g., during surgery to correct other damage resulting from the trauma. Accordingly, EGF-$X_{16}$ may be administered as a pharmaceutical composition comprising EGF-$X_{16}$ in combination with a pharmaceutically acceptable excipient. Such compositions may be aqueous solutions, emulsions, creams, ointments, suspensions, gels, liposomal suspensions, and the like. Thus, suitable excipients include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol®, vegetable oils, and the like. One may additionally include suitable preservatives, stabilizers, antioxidants, antimicrobials, and buffering agents, for example, BHA, BHT, citric acid, ascorbic acid, tetracycline, and the like. Cream or ointment bases useful in formulation include lanolin, Silvadene® (Marion), Aquaphor® (Duke Laboratories), and the like. Other topical formulations include aerosols, bandages, and other wound dressings. Alternatively, one may incorporate or encapsulate EGF-$X_{16}$ in a suitable polymer matrix or membrane, thus providing a sustained-release delivery device suitable for implantation near the site to be treated locally. Other devices include indwelling catheters and devices such as the Alzet® minipump. Ophthalmic preparations may be formulated using commercially available vehicles such as Sorbi-care® (Allergan), Neodecadron® (Merck, Sharp & Dohme), Lacrilube®, and the like. Further, one may provide EGF-$X_{16}$ in solid form, especially as a lyophilized powder. Lyophilized formulations typically contain stabilizing and bulking agents, for example human serum albumin, sucrose, mannitol, and the like. A thorough discussion of pharmaceutically acceptable excipients is available in *Remington's Pharmaceutical Sciences* (Mack Pub. Co.).

The amount of EGF-$X_{16}$ required to treat any particular disorder will of course vary depending upon the nature and severity of the disorder, the age and condition of the subject, and other factors readily determined by one of ordinary skill in the art. The appropriate dosage may be determined by one of ordinary skill by following the methods set forth below in the examples. As a general guide, about 10–1,000 ng/Kg EGF-$X_{16}$ administered i.v. or subcutaneously is effective for inhibiting gastric acid secretion. For treating wounds, EGF-$X_{16}$ may be administered locally in a gel or matrix at a concentration of about $10^{-12}$ to $10^{-9}$ M.

EXAMPLES

The examples presented below are provided as a further guide to the practitioner of ordinary skill in the art, and are not to be construed as limiting the invention in any way.

Example 1

(Preparation of EGF muteins)

Synthesis

Plasmid pEGF-Iq was constructed for use in bacterial expression by inserting the Lac repressor gene LacI$^q$ into the EcoRI site of pBR322, followed in the same orientation by tac promoter, a superoxide dismutase leader, and a chemically synthesized EGF mutein gene. One may substitute any convenient secretion leader functional in the selected host cell with essentially equivalent results.

Another plasmid (designated herein as pAB-EGFX) was constructed for use in yeast expression by inserting a GAP promoter, yeast α-factor leader, a chemically synthesized EGF mutein gene, and GAP terminator into yeast vector pAB24.

The EGF gene was prepared by cassette mutagenesis, and was synthesized by standard solid-phase methods. Polynucleotides were prepared which encoded wtEGF, φEGF, EGF-$A_{15}$, EGF-$A_{16}$, EGF-$A_{41}$, EGF-$A_{43}$, φEGF-$W_{13}$, and φEGF-$Q_{12}$.

Expression in Prokaryotes

Plasmid pEGF-Iq was transformed into competent E. coli JM107 cells and grown in L-broth (25 µg/mL Ampicillin) to saturation. A 1:100 dilution was agitated at 350 rpm and 37° C. for 3 hr. Next, choramphenicol was added to 5 µg/mL and shaking continued for 2 hr.; IPTG was then added to a final concentration of 0.1 mM to induce EGF expression, and the culture shaken at 250 rpm for 12 hr.

Cultures (1.0 L) were then centrifuged (3500 rpm, 30 rain), and the pellets gently resuspended in 100 mL ice cold buffer (1.0 M Tris-HCl, 2 mM EDTA, pH 9.0) and incubated on ice four 20 min. The suspensions were clarified by centrifugation (3500 rpm, 30 min, 4° C). The supernatants were dialyzed against 0.1 M HOAc, clarified by centrifugation, concentrated 20× (YM-2 membrane, Amicon) and reclarified.

Non-flagged muteins were purified by gel filtration (P10, BioRad) and purity confirmed by amino acid analysis. Flagged muteins were purified by dialyzing 50 mL of lysate (derived from 500 mL of culture) against $CaCl_2$ (1.0 M in PBS, pH 7.4, 2× 1.0 L), and clarified by centrifugation (25,000×g, 45 min). Samples were applied to a 1.0 mL antiflag MAb affinity chromatography column (International Biotechnology Inc.), washed with 4×1.0 mL aliquots of $CaCl_2$ (1.0 M in PBS), and eluted in 1.0 mL fractions using EDTA (2.0 mM in PBS) with a 30 min incubation at room temperature between each fraction. Analysis by native and denaturing PAGE indicated purities of >90%, with no detectable levels of intermolecular crosslinked derivatives. wtEGF, φEGF, EGF-$A_{15}$, EGF-$A_{16}$, EGF-$A_{41}$, EGF-$A_{43}$, φEGF-$W_{13}$, and φEGF-$Q_{12}$ were isolated.

Expression in Yeast

*Saccharomyces cerevisea* strain AB122 were transformed with pAB-EGFX encoding the EGF muteins described above. The yeast are grown in Leu⁻ media (850 mL yeast minimal media, with 100 mL leucine-minus supplements 10×and 40 mL of 2% glucose). The product is purified from the conditioned medium following the procedure of C. George-Nascimento et al, *Biochem* (1988) 27:797–802. Briefly, after 72–96 hours the media is collected by centrifugation and concentrated by membrane filtration using an Amicon concentrator (membrane YM2). The concentrated medium is applied to a P-10 gel filtration column (BioRad, Richmond, Calif.) and eluted with 0.1 M acetic acid. The EGF-containing fractions are pooled and concentrated, followed by reverse phase-HPLC using a semi-prep C4 column (10 mm×25 cm). The column is equilibrated with 75% A/25% B (A=5% aqueous acetonitrile with 0.05% trifluoroacetic acid: B=80% aqueous acetonitrile with 0.05% trifluoroacetic acid), and eluted with a linear gradient from 25% B to 40% B. The product is confirmed by amino acid sequencing using automated Edman degradation.

Example 2

(Determination of Receptor Affinity and Mitogenicity)

Affinity

Confluent A43 1 cells were fixed in 96-well microtiter plates using 0.05% formaldehyde for 10 min at room temperature, then washed 3× with 200 μL PBS with 0.1% bovine serum albumin (BSA).

200 μL of $^{125}$I-EGF (1 nM) or an EGF mutein of the invention (1 nM) in assay buffer was added to each well in triplicate, and incubated for 2 hr at 37° C. The wells were then washed 3× with 200 μL of PBS/0.1% BSA, detached, and counted in a gamma counter. The results are shown in Table 1.

The pH dependence was determined by adjusting the assay buffer (PBS+0.1 % BSA) to various pHs (2.7–9.0) using HCl and NaOH. Conductivity readings were taken at each pH to ensure that conductivity was in a range not affecting the receptor assay. 200 μL of $^{125}$I-EGF (1 nM) or $^{125}$I-EGF-A$_{16}$ (1 nM) in assay buffer (pH 2.7–9.0) was added to each well in triplicate, and incubated for 2 hr at 37° C. The wells were then washed 3× with 200 μL of PBS/0.1% BSA, detached, and counted in a gamma counter. The results (shown in FIG. 1) demonstrate that EGF-A$_{16}$ retains its receptor binding activity at a pH approximately 1.2 pH units lower than wild type EGF.

Mitogenicity

Mitogenicity was assayed substantially following the method described by D. J. Knauer et al, *J Biol Chem* (1984) 259:5623–31.

Human foreskin fibroblasts were obtained and frozen at the thirteenth passage. Thawed cells are trypsinized, pelleted, and resuspended in a medium containing DMEM, 5% FBS, 1 mM sodium pyruvate, 300 μg/mL L-glutamine, 100 U/mL penicillin, and 100 μg/mL streptomycin. The cells are counted using a hemocytometer and 0.4% trypan blue. The cell concentration is adjusted to 1×10$^{-5}$ cells/mL using the same medium, and dispensed onto microtiter plates (100 μL/well). The plates are incubated for 5 days in a tissue culture incubator.

EGF muteins prepared in Example 1 and native sequence EGF are dissolved to make 100 μg/mL solutions. These solutions are used to make serial dilutions of 20, 10, 5, 2.5, 1.25, 0.625, 0.3125, 0.15625, 0.078125, 0.0390625, 0.0195, and 0.00975 ng/mL. Ten μL of each dilution is added to a microtiter plate well, and the plates returned to the incubator and incubated at 37° C for 18 hours. The cells are then pulsed with $^3$H-thymidine ($^3$H-T), by adding 10 μL of $^3$H-T (100 μCi/mL) to each well, and incubating for 24 hours. The $^3$H-T is then expelled, and the plates rinsed twice with PBS. To fix the cells, the plates are then incubated twice with 5% trichloroacetic acid (TCA) for 15 minutes at room temperature, followed by incubation twice with 100% MeOH. The plates are then air-dried.

The well contents are then solubilized using 0.3 N NaOH (50 μL/well) for 30 minutes, and transferred to scintillation vials. Scintillation fluid (Ready-Solv EP, 4 mL) is then added to each vial, and the vials counted for 1 min with a 0–1,000 ($^3$H) window in a Beckman LS3801 counter. The results are shown in Table 1.

TABLE 1

| Receptor Affinity and Mitogenicity of EGF Muteins | | |
|---|---|---|
| Analog | Affinity[1] | Mitogenicity[1] |
| EFG | 100 | 100 |
| φEFG | 32 | 56 |
| EGF-A$_{15}$ | 1 | 3 |
| EGF-A$_{16}$ | 95 | 103 |
| EGF-A$_{41}$ | 0.01 | <0.4 |
| EGF-A$_{43}$ | 105 | 63 |
| φEGF-W$_{13}$ | 73 | 216 |
| φEGF-Q$_{12}$ | 154 | 286 |

[1]Expressed as a percentage of control (EGF)

What is claimed:

1. An EGF mutein, said EGF mutein selected from the group consisting of:
  (a) EGF-$A_{16}$;
  (b) EGF-$E_{11}A_{16}$;
  (c) EGF-$E_{12}A_{16}$;
  (d) EGF-$W_{13}A_{16}$;
  (e) EGF-$E_{12}W_{13}A_{16}$;
  (f) EGF-$E_{11}E_{12}A_{16}$;
  (g) EGF-$E_{11}W_{13}A_{16}$; and
  (h) EGF-$E_{11}E_{12}W_{13}A_{16}$.

2. A pharmaceutical composition, said pharmaceutical composition comprising an EGF mutein, said EGF mutein selected from the group consisting of:
  (a) EGF-$A_{16}$;
  (b) EGF-$E_{11}A_{16}$;
  (c) EGF-$E_{12}A_{16}$;
  (d) EGF-$W_{13}A_{16}$;
  (e) EGF-$E_{12}W_{13}A_{16}$;
  (f) EGF-$E_{11}E_{12}A_{16}$;
  (g) EGF-$E_{11}W_{13}A_{16}$; and
  (h) EGF-$E_{11}E_{12}W_{13}A_{16}$;
and a pharmaceutically acceptable carrier.

3. A polynucleotide, said polynucleotide encoding an EGF mutein, said EGF mutein selected from the group consisting of:
  (a) EGF-$A_{16}$;
  (b) EGF-$E_{11}A_{16}$;
  (c) EGF-$E_{12}A_{16}$;
  (d) EGF-$W_{13}A_{16}$;
  (e) EGF-$E_{12}W_{13}A_{16}$;
  (f) EGF-$E_{11}E_{12}A_{16}$;
  (g) EGF-$E_{11}W_{13}A_{16}$; and
  (h) EGF-$E_{11}E_{12}W_{13}A_{16}$.

4. A method of treating a condition selected from the group consisting of gastric ulcer, duodenal ulcer, and gastric hyperacidity, said method comprising the step of administering an effective amount of an EGF mutein, said EGF mutein selected from the group consisting of:
  (a) EGF-$A_{16}$;
  (b) EGF-$E_{11}A_{16}$;
  (c) EGF-$E_{12}A_{16}$;
  (d) EGF-$W_{13}A_{16}$;
  (e) EGF-$E_{12}W_{13}A_{16}$;
  (f) EGF-$E_{11}E_{12}A_{16}$;
  (g) EGF-$E_{11}W_{13}A_{16}$; and
  (h) EGF-$E_{11}E_{12}W_{13}A_{16}$,
to a patient in need of treatment for said condition.

5. A method of treating injury or trauma to the dermis, epidermis or cornea, said method comprising the step of administering an effective amount of an EGF mutein, said EGF mutein selected from the group consisting of:
  (a) EGF-$A_{16}$;
  (b) EGF-$E_{11}A_{16}$;
  (c) EGF-$E_{12}A_{16}$;
  (d) EGF-$W_{13}A_{16}$;
  (e) EGF-$E_{12}W_{13}A_{16}$;
  (f) EGF-$E_{11}E_{12}A_{16}$;
  (g) EGF-$E_{11}W_{13}A_{16}$; and
  (h) EGF-$E_{11}E_{12}W_{13}A_{16}$,
to a patient in need of treatment for injury or trauma to the dermis, epidermis or cornea.

* * * * *